United States Patent
Patel et al.

(10) Patent No.: US 10,220,132 B2
(45) Date of Patent: Mar. 5, 2019

(54) BIOLOGICAL FLUID FLOW CONTROL APPARATUS AND METHOD

(71) Applicant: Fenwal, Inc., Lake Zurich, IL (US)

(72) Inventors: Amit J. Patel, Algonquin, IL (US); Samantha M. Planas, Wauconda, IL (US); Kathleen M. Higginson, Mount Prospect, IL (US); Melissa A. Thill, Kenosha, WI (US); Courtney Moore, San Diego, CA (US)

(73) Assignee: Fenwal, Inc., Lake Zurich, IL (US)

( * ) Notice: Subject to any disclaimer, the term of this patent is extended or adjusted under 35 U.S.C. 154(b) by 614 days.

(21) Appl. No.: 14/577,322

(22) Filed: Dec. 19, 2014

(65) Prior Publication Data

US 2016/0175510 A1  Jun. 23, 2016

(51) Int. Cl.

| A61M 1/34 | (2006.01) |
|---|---|
| G01F 7/00 | (2006.01) |
| G05D 7/06 | (2006.01) |
| G05D 16/20 | (2006.01) |
| A61M 1/36 | (2006.01) |

(Continued)

(52) U.S. Cl.
CPC .......... *A61M 1/3496* (2013.01); *A61M 1/341* (2014.02); *A61M 1/3607* (2014.02); *A61M 1/3639* (2013.01); *A61M 5/14212* (2013.01); *A61M 5/16831* (2013.01); *A61M 5/16854* (2013.01); *G01F 7/005* (2013.01); *G05D 7/0676* (2013.01); *G05D 16/2066* (2013.01); *A61M 2005/16863* (2013.01); *A61M 2005/16868* (2013.01); *A61M 2205/18* (2013.01); *A61M 2205/3331* (2013.01);

(Continued)

(58) Field of Classification Search
CPC ............ A61M 1/3496; A61M 5/14212; A61M 5/16854; A61M 1/3639; A61M 5/16831; A61M 1/3607; A61M 2205/18; A61M 2205/50; A61M 2005/16868; A61M 2205/3331; G05D 16/2066; G05D 7/0676; G01F 7/005
See application file for complete search history.

(56) References Cited

U.S. PATENT DOCUMENTS

| 4,534,756 A | 8/1985 | Nelson |
| 4,617,014 A | 10/1986 | Cannon |

(Continued)

FOREIGN PATENT DOCUMENTS

| EP | 0248632 A2 | 9/1987 |
| EP | 0328162 A2 | 8/1989 |

(Continued)

OTHER PUBLICATIONS

European Search Report for EP Application No. 15200457 dated Apr. 22, 2016.

*Primary Examiner* — Kenneth M Lo
*Assistant Examiner* — David J Wynne
(74) *Attorney, Agent, or Firm* — Cook Alex Ltd.

(57) ABSTRACT

Apparatus, system and method are provided for controlling flow through a biological fluid processing device. Pressure of fluid flow through a flow path is monitored and flow rate in the flow path is increased or decreased based on sensed pressure levels for selected periods of time. This has particular application in controlling flow in an infusion or return flow path of an apheresis device that separates whole blood into one or more blood components.

18 Claims, 8 Drawing Sheets

(51) Int. Cl.
  *A61M 5/168* (2006.01)
  *A61M 5/142* (2006.01)
(52) U.S. Cl.
  CPC .............. *A61M 2205/3334* (2013.01); *A61M 2205/3337* (2013.01); *A61M 2205/3341* (2013.01); *A61M 2205/50* (2013.01)

(56) References Cited

U.S. PATENT DOCUMENTS

| | | | |
|---|---|---|---|
| 4,743,228 A | 5/1988 | Butterfield | |
| 4,863,425 A | 9/1989 | Slate | |
| 4,882,575 A | 11/1989 | Kawahara | |
| 5,096,385 A | 3/1992 | Heinz | |
| 5,178,603 A * | 1/1993 | Prince | A61M 1/30 604/6.01 |
| 5,501,665 A | 3/1996 | Jhuboo | |
| 5,690,831 A | 11/1997 | Kenley | |
| 5,795,317 A | 8/1998 | Brierton | |
| 5,935,106 A | 8/1999 | Olsen | |
| 6,325,775 B1 | 12/2001 | Thom | |
| 6,423,035 B1 | 7/2002 | Das | |
| 6,485,465 B2 | 11/2002 | Moberg | |
| 6,558,347 B1 | 5/2003 | Jhuboo | |
| 6,585,675 B1 * | 7/2003 | O'Mahony | A61M 1/34 604/4.01 |
| 6,689,083 B1 | 2/2004 | Gelfand | |
| 6,691,047 B1 | 2/2004 | Fredericks | |
| 6,723,062 B1 | 4/2004 | Westberg | |
| 6,790,195 B2 | 9/2004 | Steele | |
| 6,949,079 B1 | 9/2005 | Westberg | |
| 7,108,672 B2 | 9/2006 | Steele | |
| 7,147,613 B2 | 12/2006 | Burbank | |
| 7,169,352 B1 | 1/2007 | Felt | |
| 7,172,570 B2 | 2/2007 | Cavalcanti | |
| 7,195,607 B2 | 3/2007 | Westberg | |
| 7,462,161 B2 | 12/2008 | O'Mahony | |
| 7,513,882 B2 | 4/2009 | Felt | |
| 7,608,053 B2 | 10/2009 | Felt | |
| 7,648,477 B2 | 1/2010 | Vinci | |
| 7,674,237 B2 | 3/2010 | O'Mahony | |
| 7,749,184 B2 | 7/2010 | Cavalcanti | |
| 7,780,618 B2 | 8/2010 | Felt | |
| 7,824,354 B2 | 11/2010 | Vinci | |
| 7,955,289 B2 | 6/2011 | O'Mahony | |
| 7,993,297 B2 | 8/2011 | Vinci | |
| 8,088,090 B2 | 1/2012 | Felt | |
| 8,105,260 B2 | 1/2012 | Tonelli | |
| 8,182,461 B2 | 5/2012 | Pope | |
| 8,241,237 B2 | 8/2012 | Gatti | |
| 8,267,881 B2 | 9/2012 | O'Mahony | |
| 8,388,567 B2 | 3/2013 | Rovatti | |
| 8,603,021 B2 | 12/2013 | Levin | |
| 8,647,289 B2 | 2/2014 | Pages | |
| 8,676,512 B2 | 3/2014 | Balschat | |
| 8,702,637 B2 | 4/2014 | Pages | |
| 8,702,638 B2 | 4/2014 | O'Mahony | |
| 8,771,215 B2 | 7/2014 | Tonelli | |
| 8,900,213 B2 | 12/2014 | Pope | |
| 2002/0016569 A1 | 2/2002 | Critchlow | |
| 2005/0230313 A1 * | 10/2005 | O'Mahony | A61M 1/34 210/645 |
| 2009/0043240 A1 * | 2/2009 | Robinson | A61B 5/14532 604/6.11 |
| 2010/0179467 A1 | 7/2010 | Gunther et al. | |
| 2011/0178453 A1 * | 7/2011 | Pages | A61M 1/3472 604/6.02 |
| 2012/0053501 A1 * | 3/2012 | Brown | A61M 1/3672 604/6.07 |
| 2012/0150089 A1 | 6/2012 | Penka | |
| 2013/0146148 A1 * | 6/2013 | Smirnov | F17D 1/16 137/13 |
| 2014/0148750 A1 | 5/2014 | Pages | |
| 2014/0231350 A1 | 8/2014 | Levin | |
| 2015/0045712 A1 | 2/2015 | Ninomiya | |
| 2015/0354473 A1 * | 12/2015 | Ensan | F02D 19/0628 123/526 |

FOREIGN PATENT DOCUMENTS

| | | |
|---|---|---|
| EP | 0328163 B1 | 8/1989 |
| EP | 1126885 A1 | 8/2001 |
| EP | 1129291 B1 | 9/2001 |
| EP | 1135187 B1 | 9/2001 |
| EP | 1188454 B1 | 3/2002 |
| EP | 1339315 B2 | 9/2003 |
| EP | 1458431 B1 | 9/2004 |
| EP | 1529546 B1 | 5/2005 |
| EP | 1590018 B1 | 11/2005 |
| EP | 1728526 A1 | 12/2006 |
| EP | 1738784 A1 | 1/2007 |
| EP | 1773427 B2 | 4/2007 |
| EP | 2095835 A1 | 9/2009 |
| EP | 2142235 B1 | 1/2010 |
| EP | 2268339 B1 | 1/2011 |
| EP | 2420264 A2 | 2/2012 |
| EP | 2445545 B1 | 5/2012 |
| EP | 2823833 A1 | 1/2015 |
| WO | WO 87/05225 A | 9/1987 |
| WO | WO 92/02264 | 2/1992 |
| WO | WO 01/17584 A1 | 3/2001 |
| WO | WO 01/17604 A1 | 3/2001 |
| WO | WO 01/18396 A1 | 3/2001 |
| WO | WO 01/72357 A2 | 10/2001 |
| WO | WO 01/89599 A2 | 11/2001 |
| WO | WO 02/35979 A2 | 5/2002 |
| WO | WO 02/38204 A2 | 5/2002 |
| WO | WO 02/47609 A2 | 6/2002 |
| WO | WO 03/055542 A1 | 7/2003 |
| WO | WO 2004067064 A1 | 8/2004 |
| WO | WO 2006011009 A2 | 2/2006 |
| WO | WO 2007059476 A2 | 5/2007 |
| WO | WO 2008125894 A1 | 10/2008 |
| WO | WO 2009080258 A1 | 7/2009 |
| WO | WO 2009129140 A1 | 10/2009 |
| WO | WO 2010149408 A1 | 12/2010 |
| WO | WO 02/022187 | 3/2012 |
| WO | WO 2013132923 A1 | 9/2013 |
| WO | WO 2014/083448 | 6/2014 |

* cited by examiner

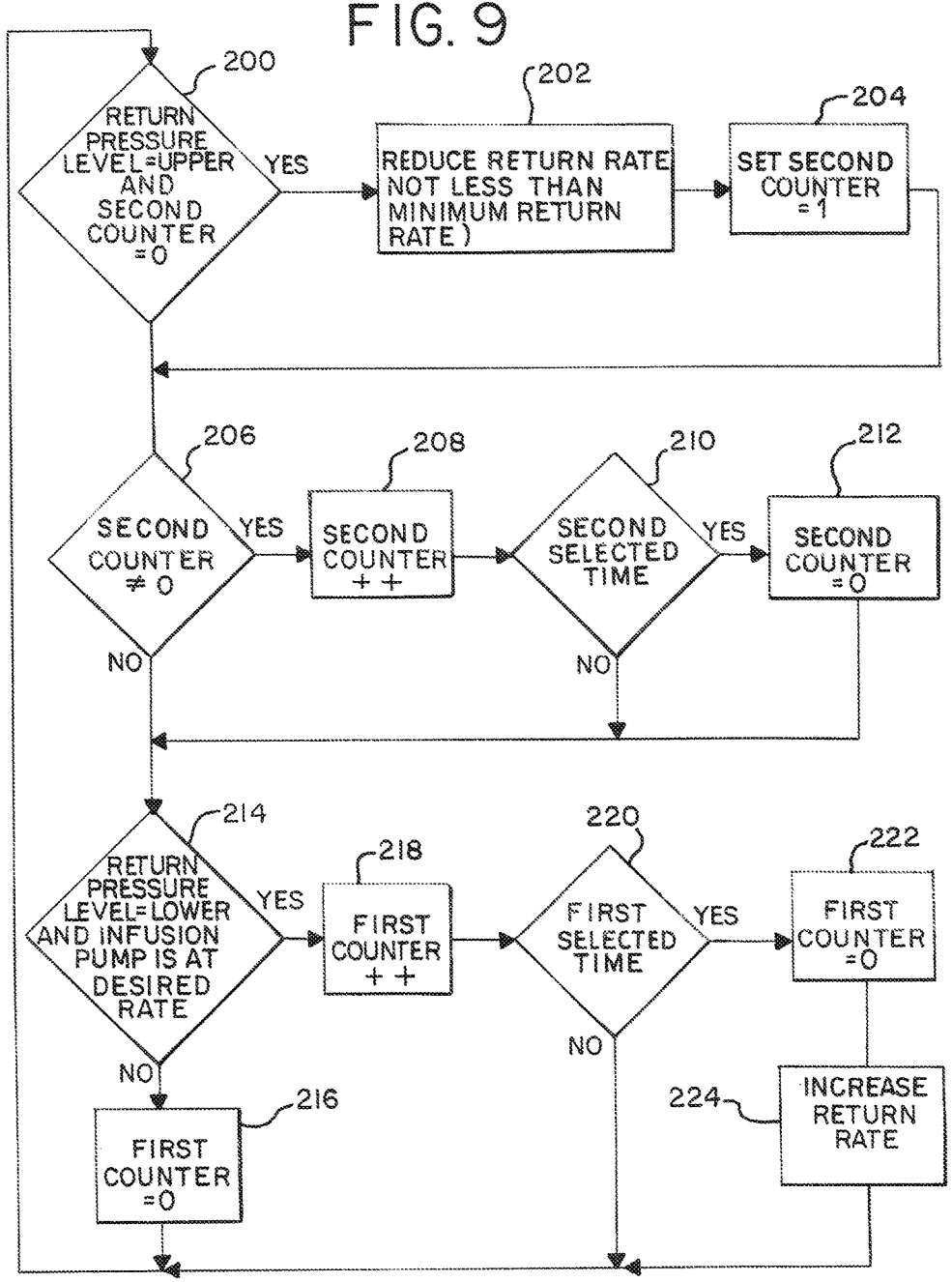

BIOLOGICAL FLUID FLOW CONTROL APPARATUS AND METHOD

BACKGROUND

Field of the Disclosure

The subject matter of this application relates generally to biological fluid processing systems and methods such as biological fluid separation systems and methods. More particularly, the subject matter relates to methods, devices and systems for controlling fluid flow and, more particularly, for controlling flow rates and pressures in a fluid flow path such as a return or infusion flow path that may be connected to a human subject.

Description of Related Art

Various blood processing systems now make it possible to collect and/or process particular blood constituents, instead of whole blood, from a blood source such as, but not limited to, a container of previously collected blood or other living or non-living source. Typically, in such systems, whole blood is drawn from a blood source, a particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into one or more of its constituents (e.g., red cells, platelets, and plasma) by processing through a disposable fluid flow circuit that is associated with a durable, reusable device that controls the processing of fluid through the flow circuit by a variety of pumps, valves, sensors and the like that operate on the fluid flow circuit. Typical separation techniques include centrifugation, such as in the AMICUS® separator from Fenwal, Inc. of Lake Zurich, Ill., or other centrifugal separation devices, or membrane separation such as a spinning membrane-type separator, such as the AUTOPHERESIS-C® and AURORA® devices from Fenwal, Inc.

While the above refers to apheresis systems in particular, the present subject matter, as seen below, is not limited to such whole blood apheresis applications but may include systems for processing blood components or other biological fluid components. With reference to apheresis systems, as noted above, blood components that are not collected are typically returned to the source or subject, such as a patient or donor. These may include concentrated red cells, plasma, platelets or some combination of these. Also, it is common to infuse into the donor or patient a replacement fluid, such as saline, to replace the volume of the blood components that have been removed and not returned. To this end, such systems include a fluid flow path that communicates with the source or subject, such as but not limited to a human donor or patient, for directing or returning blood, blood components or other fluids to the subject. The fluid flow path is usually in the form of flexible plastic flow tubing terminating in a needle or other access device that is inserted into a subject's (human donor's or patient's) vein.

So as not unduly to extend the time required of a donor or patient in an apheresis procedure, it is beneficial for the flow rate in the return or infusion fluid flow path to be as fast as reasonably possible. However, the flow rate is constrained by several factors. For example, it may be desired not to exceed certain pressure thresholds or limits that may be potentially detrimental or uncomfortable for the subject.

Another complicating factor is fluid flow path occlusions, which may lead to occlusion alarms. Infusion of fluid into a donor or patient sometimes encounters flow blockages or occlusions that may be physiologically related, such as clotting, blood vessel limits or needle position within the subject's vein, or due to equipment related issues such as inadvertently crimped infusion flow tubing, or the like. In prior systems, such occlusions are commonly detected by the processing system from increased fluid pressure within the infusion fluid flow path, and typically resulted in an alarm condition being generated to alert the system operator of the occlusion. This alarm condition was often accompanied by automatic stoppage of the apheresis procedure and/or the infusion fluid flow to the subject. Of course, the requirement for operator intervention to identify and clear the source of the alarm and the temporary interruption in the procedure combine to create potentially increased procedure time and greater burden on the operator, who may be overseeing the operation of several apheresis procedures at the same time. As a result, there is continuing desire to provide apheresis and other similar biological fluid processing systems and methods that will tend to reduce the incidence of unnecessary occlusion alarms while also limiting procedure time delays. The present subject matter relates to such methods, devices and systems.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto. These and other aspects may be found in the description, drawings, claims and the additional listing of various aspects set forth later in this specification.

For illustrative summary purposes, in accordance with one aspect of the present subject matter, a method is provided for controlling flow through a biological fluid processing device (such as a blood apheresis device) fluid flow path. The fluid may be, for example, blood components being returned to a donor, replacement fluid, a combination of both and/or another infusion fluid. In this description, references to infusion and return may be used interchangeably and include but are not limited to apheresis systems where the subject is typically a living donor. The method includes: (1) flowing fluid through the fluid flow path at a flow rate; monitoring the pressure of fluid flowing in the fluid flow path; and increasing the flow rate of fluid in the fluid flow path by a first selected amount if the monitored pressure is below a first pressure level for at least a first amount of time, with the first pressure level being below a maximum allowed pressure level; and (2) decreasing the fluid flow rate in the fluid flow path by a second selected amount if the monitored pressure is above a second pressure level for a second amount of time, with the second pressure level being below the maximum allowed pressure level and above the first pressure level.

In accordance with another aspect of the present subject matter, a durable biological fluid processing device may be provided for processing biological fluid in a disposable fluid processing flow circuit of the type including a fluid flow path for directing fluid flow from the processing circuit to a subject. The device includes a pump for pumping fluid through the fluid flow path, a pressure sensor for monitoring fluid pressure in the flow path and a controller cooperatively associated with the pump and the pressure sensor for controlling the flow rate and pressure of fluid flowing through the fluid flow path. The controller is configured to, at least: monitor the pressure of fluid flowing in the fluid flow path, increase the flow rate of fluid in the fluid flow path by a first selected amount if the monitored pressure is below a first pressure level for at least a first amount of time, the first pressure level being a maximum allowed pressure level; and decrease the fluid flow rate in the fluid flow path by a second selected amount if the monitored pressure is above a second pressure level for a second amount of time, the second pressure level being below the maximum allowed pressure level and above the first pressure level. As described below, the return flow rate may also be limited so that it cannot be increased to exceed a maximum flow rate. As an example, the maximum flow may be the lesser of (i) a desired flow rate set by the operator and (ii) a flow rate that results in the maximum allowable flow rate of anticoagulant, e.g., citrate, being returned to a donor.

In accordance with yet another aspect of the present subject matter, a system may be provided including a durable biological fluid processing device in accordance with the above aspect in combination and cooperation with a disposable fluid processing flow circuit of the type including a fluid flow path for directing fluid flow from the processing circuit to a subject

BRIEF DESCRIPTION OF THE DRAWINGS

FIG. 9 is a flow chart illustrating in greater detail a potential method of fluid flow control in an infusion or return fluid flow path for infusing fluid into a subject such as a donor or patient in accordance with another aspect of the present subject matter.

DESCRIPTION OF THE ILLUSTRATED EMBODIMENTS

The embodiments disclosed herein are for the purpose of providing an exemplary description of the present subject matter. They are only exemplary, however, and the present subject matter may be embodied in various forms. Therefore, specific details disclosed herein are not to be interpreted as limiting the subject matter as defined in the accompanying claims.

Figure 1:
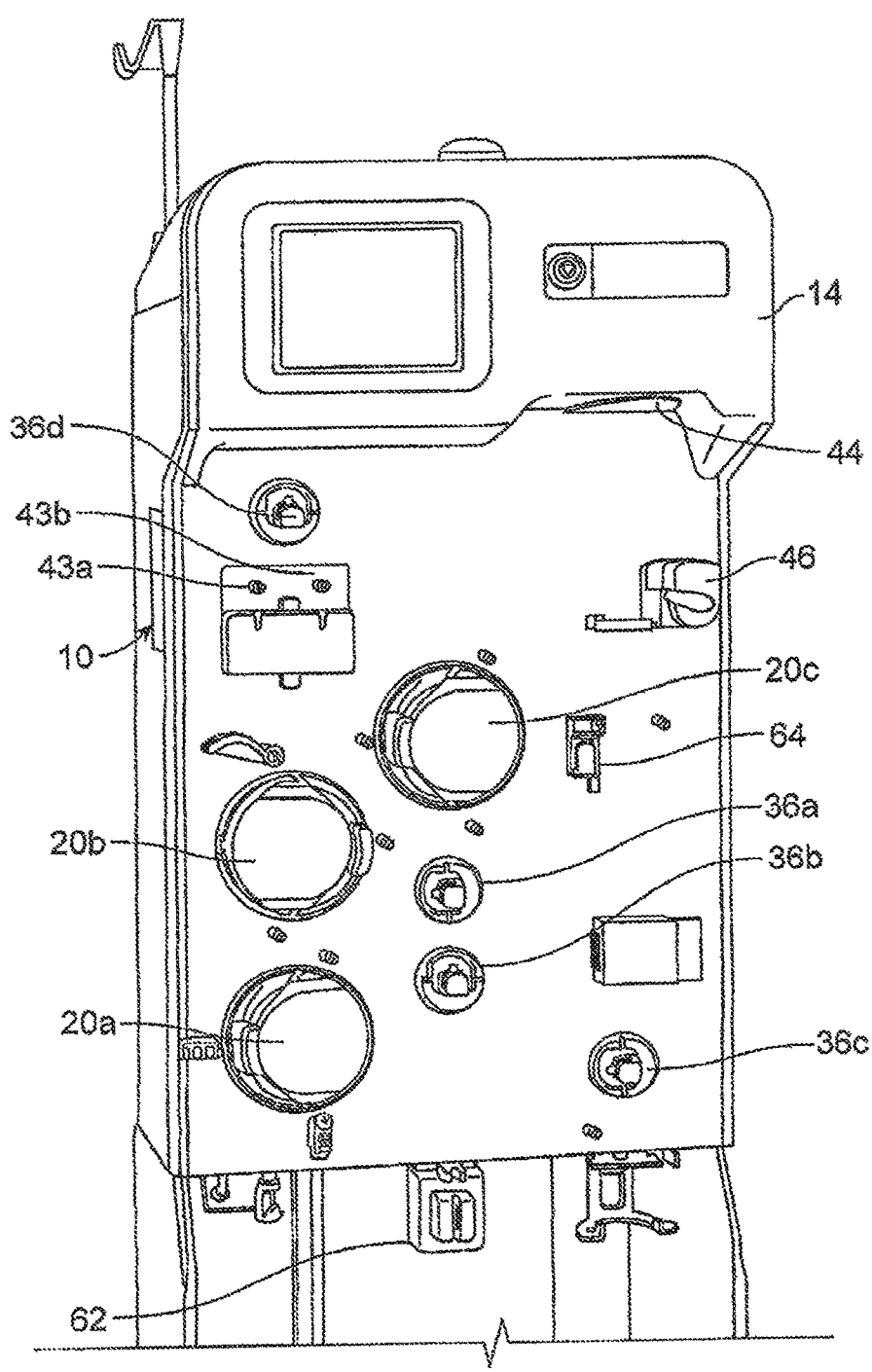
FIG. 1 is a front perspective view of an exemplary biological fluid processing system and, more specifically, a fluid separation system such as an apheresis system according to an aspect of the present disclosure.
Figure 2:
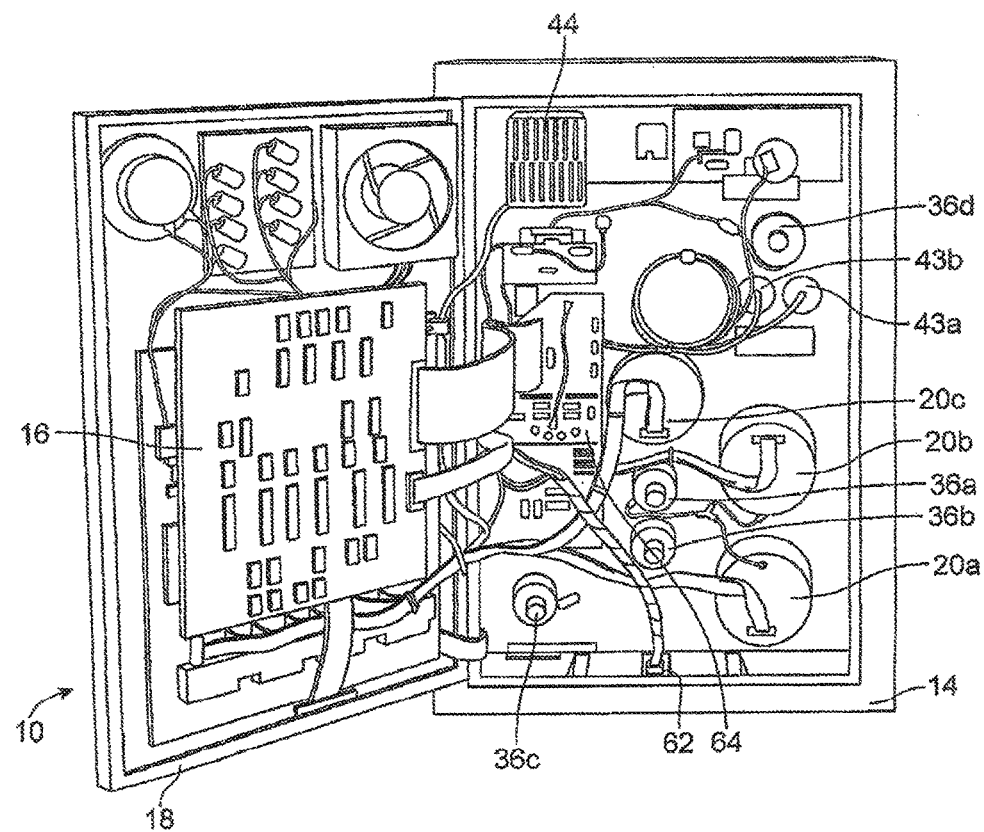
FIG. 2 is a rear perspective view of the fluid separation system of FIG. 1, with a rear door of a cabinet or housing thereof in an open position.
Figure 3:
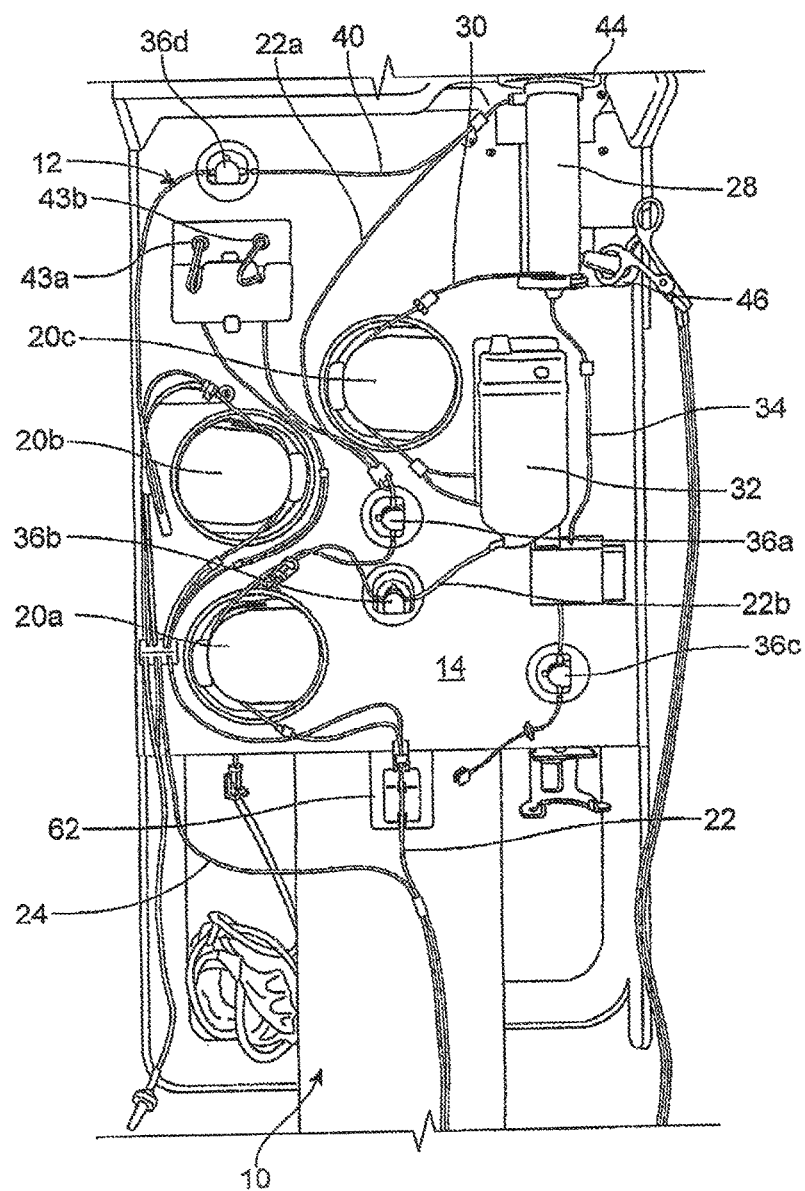
FIG. 3 is a front perspective view of the fluid separation system of FIG. 1, with a fluid flow circuit associated therewith.

According to an aspect of the present disclosure, a durable or reusable fluid separation system is used in combination with a separate fluid flow circuit (which may be disposable) to separate a fluid into two or more constituent parts. FIGS. 1 and 2 illustrate an exemplary fluid separation system 10, while FIG. 3 illustrates an exemplary fluid flow circuit 12 mounted onto the fluid separation system 10, but it should be understood that the illustrated fluid separation system 10 and fluid flow circuit 12 are merely exemplary of such systems and circuits and that differently configured fluid separation systems and fluid flow circuits may be provided without departing from the scope of the present disclosure.

The system 10 of FIG. 1 is configured for processing whole blood, but it may be used to process other biological fluids The fluid may come from any fluid source and be returned to any recipient, which may be the same as or different from the fluid source. In one embodiment, the fluid source/recipient is a living donor or patient (e.g., a human blood donor), while in other embodiments the fluid source, subject and/or fluid recipient may be a non-living source/recipient (e.g., a blood bag or other fluid container).

Figure 5:
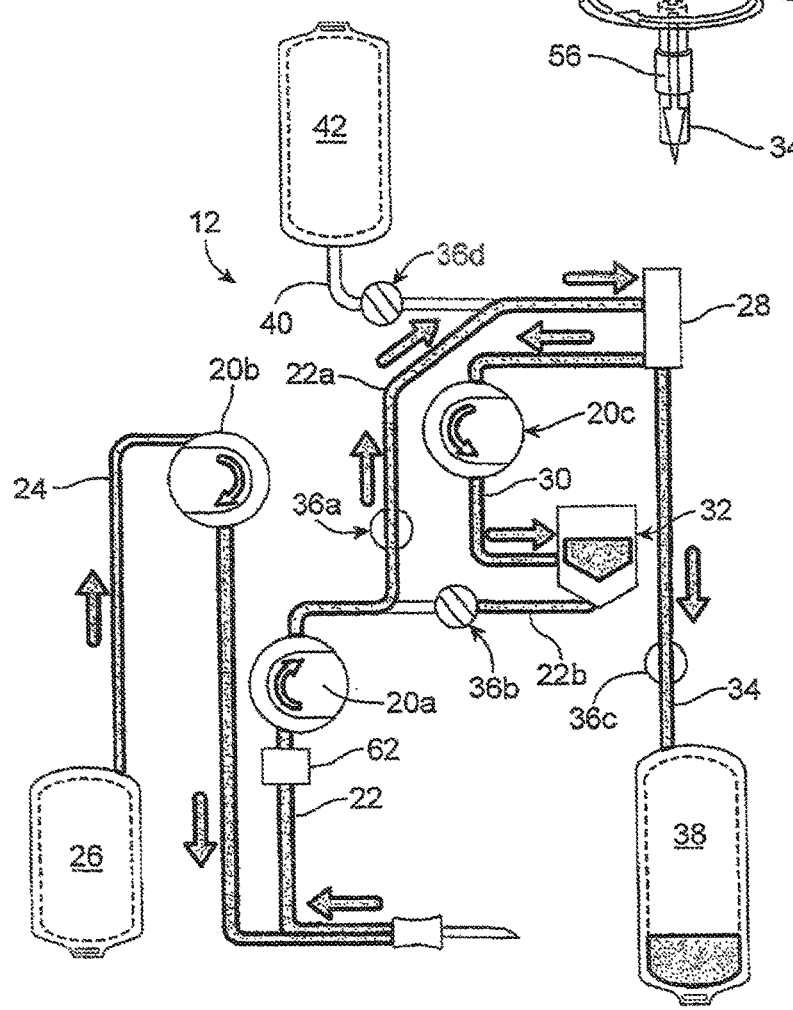
FIG. 5 is a schematic view of the fluid flow circuit and fluid separation system of FIG. 3, in a fluid draw mode.
Figure 6:
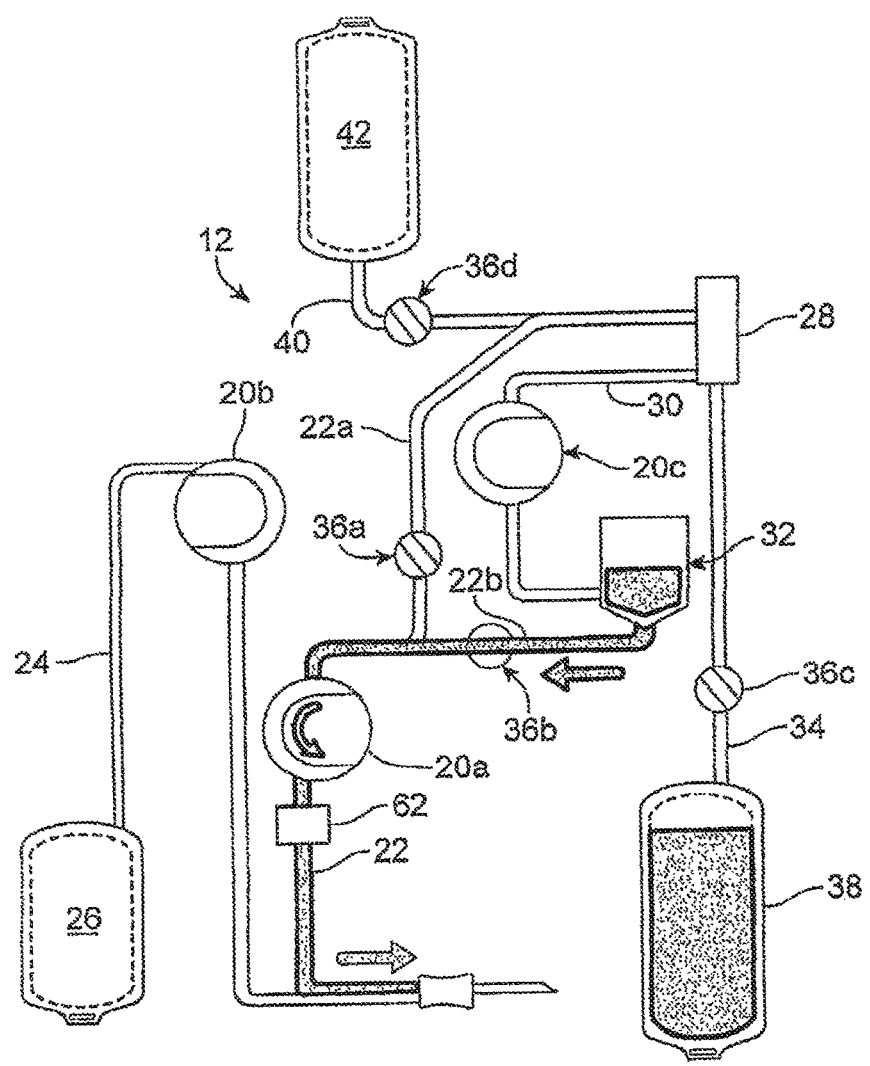
FIG. 6 is a schematic view of the fluid flow circuit and fluid separation system of FIG. 3, in a fluid return mode.

The illustrated system 10 includes a cabinet or housing 14, with several components positioned outside of the cabinet 14 (e.g., associated with a front wall or surface or panel of the cabinet 14) and additional components (including a central processing unit or controller 16, such as programmable micro-processor based controller) and interconnects positioned inside of the cabinet 14, which may be accessed by opening a rear door 18 of the system 10, as shown in FIG. 2. "Controller" is used generally and may include any higher or lower level processors that are part of the overall control or operation of the system or process, whether combined in a single processing unit or separate discrete components or structures. Among the system components positioned on the outside of the cabinet 14, one or more pumps or pump stations 20a-20c may be provided, with the pumps 20a-20c configured to accommodate tubing lines of the fluid flow circuit 12. One of the pumps 20a may be provided as a source/recipient access pump, which may be associated with a source/recipient access or fluid flow path or line 22 of the fluid flow circuit 12 and operates to draw fluid from a fluid source (FIG. 5) and to return fluid to a fluid recipient (FIG. 6). Another one of the pumps 20b may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a fluid separation module or chamber 28 of the fluid flow circuit 12. A third pump 20c may be provided to draw a return fluid (i.e., a fluid constituent to be returned or infused into a fluid recipient) from the fluid separation chamber 28 and direct it into a return fluid reservoir 32 after the fluid has been separated into a return fluid and a collection fluid in the fluid separation chamber 28. The return fluid pump 20c may also be referred to as a red cell pump in the illustrated embodiment, as red cell concentrate may be a typical fluid returned to a donor in a procedure where the primary collection target is plasma.

In the illustrated embodiment, the pumps 20a-20c are rotary peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a collection fluid outlet line 34 of the fluid flow circuit 12 to draw a collection fluid from the fluid separation chamber 28 after the fluid from the fluid source has been separated into a return fluid and a collection fluid. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps or valves 36a-36d associated with the tubing lines of the fluid flow circuit 12. The clamps or valves 36a-36d may be variously configured and operate to selectively allow and prevent fluid flow through the associated tubing line. In the illustrated embodiment, one clamp or valve 36a may be provided as a fluid source/recipient clamp, which may be associated with a draw branch 22a of the source/recipient access line 22 of the fluid flow circuit 12 to allow (FIG. 5) or prevent (FIG. 6) the flow of fluid through the draw branch 22a of the source/recipient access line 22. Another one of the clamps or valves 36b may be provided as a reinfusion clamp or valve, which may be associated with a reinfusion branch 22b of the source/recipient access line 22 downstream of a return fluid reservoir 32 of the fluid flow circuit 12 to allow (FIG. 6) or prevent (FIG. 5) the flow of return or replacement fluid through the infusion branch 22b. A third clamp or valve 36c may be provided as a collection fluid clamp or valve, which may be associated with the collection fluid outlet line 34 to allow (FIG. 5) or prevent (FIG. 6) the flow of collection fluid through the collection fluid outlet line 34 and into a collection fluid container 38. A fourth clamp or valve 36d may be provided as a replacement fluid clamp or valve, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps or valves may also be provided without departing from the scope of the present disclosure.

The illustrated system 10 further includes one or more pressure sensors 43a and 43b of conventional design that may be associated with the fluid flow circuit 12 to monitor the pressure within one or more of the tubing lines of the fluid flow circuit 12 during operation of the pumps 20a-20c and clamps or valves 36a-36d. In one embodiment, one pressure sensor 43a may be associated with a tubing line that draws fluid (for example whole blood) from a fluid source and/or directs processed or replacement fluid (for example blood components, such as red cell concentrate, and/or saline) to a fluid recipient or subject, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller 16 that are indicative of the pressure within the tubing line or lines being monitored by the pressure sensor 43a and/or 43b. As described in more detail later, if the controller 16 determines that an undesired or improper pressure is present within the fluid flow circuit 12 (e.g., a high pressure due to an occlusion of one of the tubing lines), then the controller 16 may generate an alarm and/or instruct one or more of the pumps 20a-20c and/or one or more of the clamps or valves 36a-36d to act so as to alleviate the improper pressure condition (e.g., by changing the fluid flow rate, reversing the direction of operation of one of the pumps 20a-20c and/or opening or closing one of the clamps or valves 36a-36d). Additional or alternative pressure sensors may also be provided without departing from the scope of the present disclosure.

Figure 4:
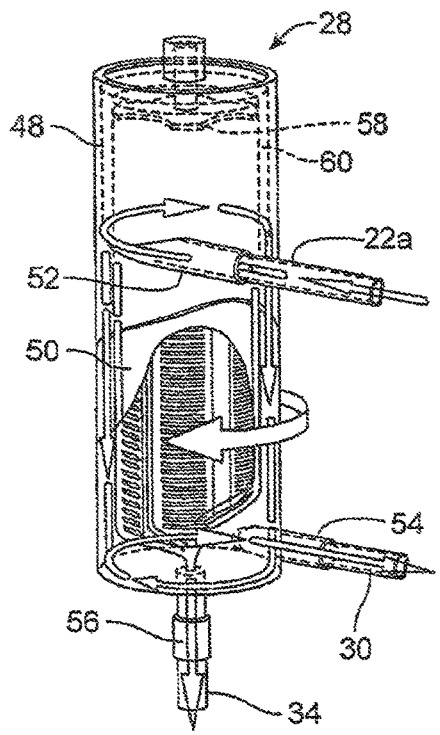
FIG. 4 is a front perspective view of a biological fluid (for example blood) separation chamber of the fluid flow circuit of FIG. 3, with a portion thereof broken away for illustrative purposes.

The illustrated system 10 may also include a separation actuator 44 that interacts with a portion of the fluid separation chamber 28 to operate the fluid separation chamber 28. A chamber lock 46 may also be provided to hold the fluid separation chamber 28 in place with respect to the system cabinet 14 and in engagement with the separation actuator 44. The configuration and operation of the separation actuator 44 depends upon the configuration of the fluid separation chamber 28. In the illustrated embodiment, the fluid separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1, all of which are hereby incorporated herein by reference. If provided as a spinning membrane-type separator, the fluid separation chamber 28 may include a tubular housing 48 (FIG. 4), with a microporous membrane 50 positioned therein. An inlet 52 allows a fluid from a fluid source to enter into the housing 48 (via the draw branch 22a of the source/recipient access line 22), while a side outlet 54 allows return fluid to exit the housing 48 (via the return fluid outlet line 30) and a bottom outlet 56 allows collection fluid to exit the housing 48 (via the collection fluid outlet line 34) after the fluid from the fluid source has been separated into return fluid and collection fluid.

In the illustrated embodiment, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the return fluid away from the membrane 50 to exit the fluid separation chamber 28 via the side outlet 54, while the collection fluid passes through the membrane 50 toward the central axis of the housing 48 to exit the fluid separation chamber 28 via the bottom outlet 56. In one embodiment, whole blood from a blood source is separated into cellular blood components (return fluid) and substantially cell-free plasma (collection fluid). It should be understood that the present disclosure is not limited to a particular fluid separation chamber and that the illustrated and described fluid separation chamber 28 is merely exemplary. For example, in other embodiments, a differently configured spinning membrane-type fluid separation chamber may be employed (e.g., one in which the membrane 50 is mounted on an inside surface of the housing 48 or on both the rotor 58 and an inside surface of the housing 48 and facing the gap 60), or a centrifugal separation chamber or other design without departing from the scope of the present disclosure.

The illustrated membrane material may be formed into a sheet or film using any suitable techniques to define the membrane 50 that is to be mounted onto the rotor 58 of the fluid separation chamber 28. The dimensions and configuration of the membrane 50 may vary without departing from the scope of the present disclosure, but in one embodiment a membrane 50 such as described above, and used for separation of whole blood into plasma and cellular components may have a thickness in the range of approximately 5 μm to approximately 1000 μm (preferably in the range of approximately 25 μm to approximately 200 μm), with a mean pore size in the range of approximately 0.2 μm to approximately 200 (preferably in the range of approximately 0.5 μm to approximately 10 μm and more preferably in the range of approximately 0.6 μm to approximately 5 μm). The porosity of the membrane 50 may also vary, such as from approximately 1% to approximately 90%, but preferably in the range of approximately 50% to approximately 80% to produce a membrane 50 that passes fluid therethrough at a relatively high rate while being sufficiently strong to withstand the forces applied to it by the spinning rotor 58 and fluid contact during a separation procedure.

Figure 7:
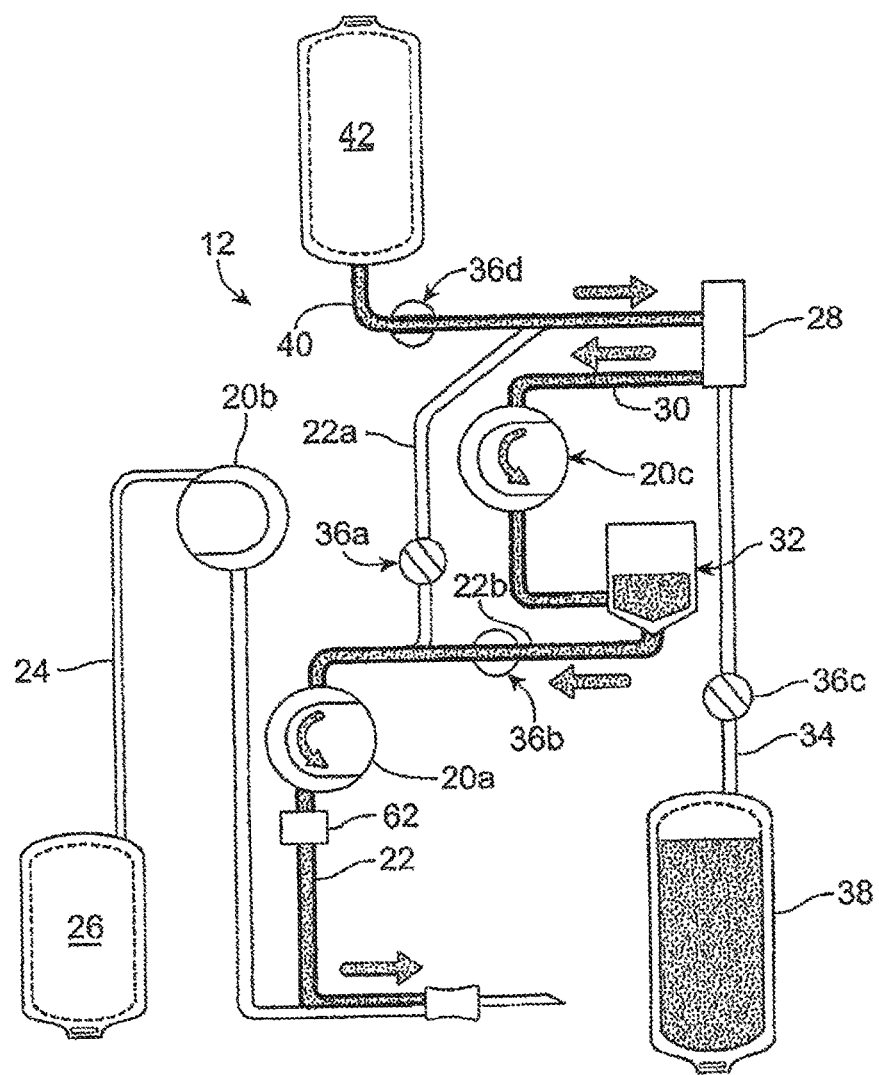
FIG. 7 is a schematic view of the fluid flow circuit and fluid separation system of FIG. 3, in a fluid return mode in which the return fluid is a replacement fluid, such as saline.

According to one method of using the fluid separation system 10 and fluid flow circuit 12, a fluid is drawn from a fluid source into the fluid separation chamber 28, or a temporary holding chamber, during a draw phase or mode (FIG. 5), where it is separated into return fluid (e.g., cellular blood components) and collection fluid (e.g., substantially cell-free plasma). The collection fluid is retained by the system 10, while the return fluid is temporarily retained and returned to the fluid source during a return or infusion phase or mode (FIG. 6). FIG. 7 shows an exemplary phase or mode in which replacement fluid (e.g., saline) is directed to the fluid recipient, either alone or with an amount of return/processed fluid. In the phase of FIG. 7, the clamp or valve 36d associated with the replacement fluid line 40 is opened to allow replacement fluid to flow out of the replacement fluid source 42. The clamp or valve 36a associated with the draw branch 22a of the source/recipient access line 22 may be in a closed condition to prevent fluid flow therethrough, such that the replacement fluid is directed into the fluid separation chamber 28. The replacement fluid is pulled out of the fluid separation chamber 28 and into the return fluid reservoir 32 by operation of the pump 20c associated with the return fluid outlet line 30. If there is any return fluid in the return fluid reservoir 32, then the replacement fluid mixes with the return fluid prior to being pumped to the fluid recipient by the pump 20a associated with the fluid recipient line 22, otherwise the replacement fluid alone may be pumped to the fluid recipient. In one embodiment, the replacement fluid return mode of FIG. 7 is carried out only once, as a final return phase (e.g., when the amount of return fluid in the return fluid reservoir 32 is at a sufficiently low level) in which a mixture of return fluid and replacement fluid is returned to the fluid recipient. This may be advantageous to ensure that all of the return fluid in the return fluid reservoir 32 (along with any remaining in the fluid separation chamber 28) is rinsed out of the return fluid reservoir 32 and pumped to the fluid recipient.

In other embodiments, the replacement fluid return mode of FIG. 7 may be carried out at other times, such as earlier in the procedure, at multiple scheduled times during a procedure, and/or at any time upon a request from the operator and/or using a different path between the replacement fluid source 42 and the fluid recipient. For example, it may be advantageous for the replacement fluid to bypass the fluid separation chamber and the return fluid reservoir 32 if the replacement fluid is being pumped to a fluid recipient earlier in the procedure. In this case, the clamp or valve 36d associated with the replacement fluid line 40 and the clamp or valve 36a associated with the draw branch 22a of the source/recipient access line 22 may be opened to allow fluid flow therethrough, with the clamp or valve 36b associated with the reinfusion branch 22b in a closed condition to prevent fluid flow therethrough. The pump 20a associated with the fluid recipient line 22 may be activated (with the other two pumps 20b and 20c inactive) to draw replacement fluid out of the replacement fluid source 42 and through the replacement fluid line 40, the draw branch 22a, and finally the source/recipient access line 22 to the fluid recipient.

In one embodiment, the draw and return phases are repeatedly alternated (drawing from the fluid source, separating the fluid from the fluid source into return fluid and collection fluid, and then pumping the return fluid and/or a replacement fluid to the fluid source or a different recipient) until a target (e.g., a particular amount of collection fluid) is achieved. All of the draw phases and all of the return phases may be identical or may differ from each other. For example, a final draw phase may draw less fluid from the fluid source than the previous draw phases and a final return phase may infuse a combination of return fluid and replacement fluid to the fluid recipient, whereas the previous return phases pump might only return fluid to the fluid recipient.

Infusion Process Control

Flow control of the return or infusion of the return fluid and/or replacement fluid or other fluid through the fluid flow path 22 is managed by the controller 16 (which can include any higher or lower level processors that are part of the an overall control or operation of the system or process), which is configured or programmed using conventional techniques to control the pumps, valves and related hardware and sensors to carry out the method described.

Figure 8:
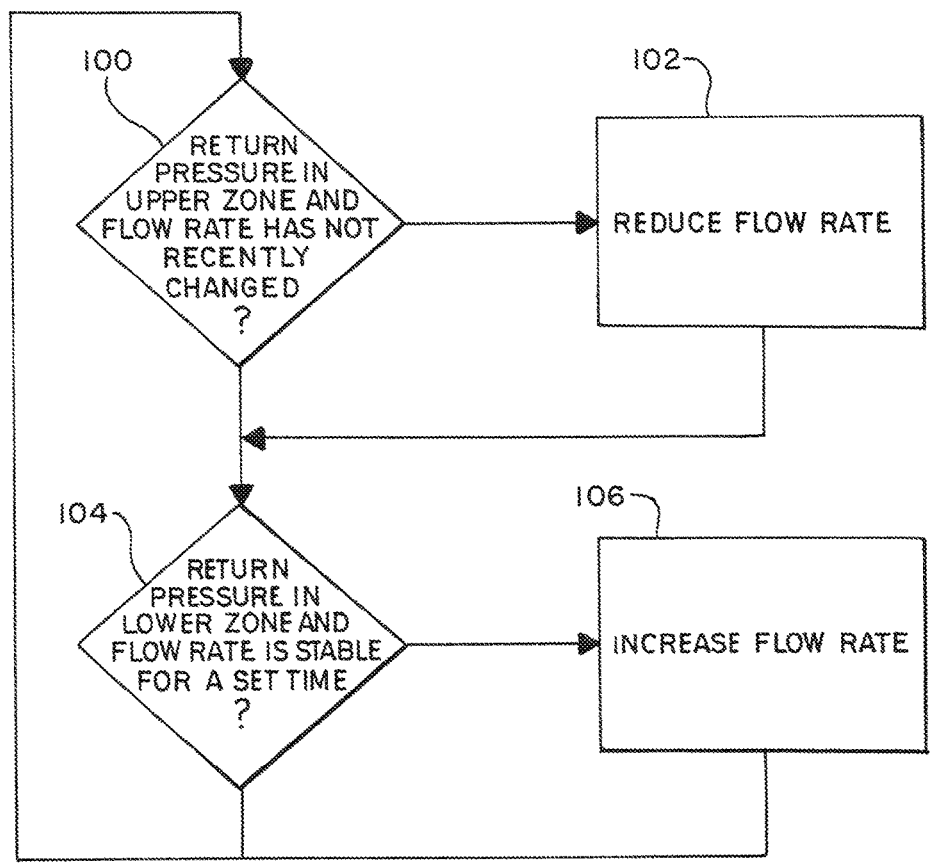
FIG. 8 is a flow chart illustrating a method of fluid flow control in an infusion or return fluid flow path for infusing fluid into a subject such as a donor or patient in accordance with one aspect of the present subject matter.

As illustrated in the flow chart of FIG. 8, the control of return or infusion flow through the flow path or line 22 employs a time-history of pressure within the flow path (as sensed by pressure sensor 43a) to control and adjust the fluid flow rate and pressure in the flow path 22 in a manner that will tend to impact procedure time (e.g., reduce or increase) and/or preferably reduce the number of occlusion alarms. More specifically, in accordance with one aspect, a plurality of pressure levels is established. In the illustrated system and method, there are at least three such pressure levels that are established for flow of fluid through the flow path 22 to the subject or source—a lower or first pressure level, an upper or second pressure level that is higher than the first level and a maximum or alarm pressure level that is greater than the upper or second level. It should be noted that this does not preclude or exclude the setting of other pressure levels for other purposes.

The maximum or alarm pressure level is first selected or assigned. For example, when the fluid flow path returns fluid to a human subject or donor, the maximum or alarm pressure level may be based on a maximum allowable pressure for the recipient's vein into which the fluid flows. The lower (or first) pressure level is selected or assigned and is less than the maximum level. Below the first or lower pressure level, flow rates can be adjusted or increased without immediate concern for unduly increasing fluid flow pressure relative to the maximum level. The upper (or second) pressure level is selected or assigned and is less than the maximum level but may be relatively nearer to or approaching the maximum level as compared to the lower level.

The overall flow pressure range is therefore divided into three ranges or zones: (1) a lower pressure range or zone below the lower (or first) pressure level, and within which fluid flow rates in the flow path 22 can be adjusted or increased without immediate concern for unduly increasing pressure relative to the maximum level (this may be referred to as a "good" pressure range); (2) an upper pressure range or zone between the upper (or second) and maximum pressure levels, where the pressure is significantly nearer to the maximum or alarm level and flow rate decreases may be appropriate to reduce the risk of triggering an alarm condition (this may sometimes be referred to as a "bad" pressure range as it is nearer to the maximum alarm level, although this terminology does not mean that the pressure in this range is harmful to the subject or that an alarm condition will necessarily be generated) and (3) an intermediate or medium pressure range or zone between the lower and upper ranges, that provides a buffer range that can accommodate pressure increases without unduly nearing the maximum or alarm level.

In the illustrated embodiment, the maximum or alarm pressure level or threshold may be based in part on the viscosity or type of fluid flowing through the flow path. For example, for pumping relatively viscous fluid containing blood cellular components through the flow path 22, such as red cell concentrate, a higher maximum pressure limit is selected or assigned as compared to fluid that is substantially free of cellular components, such as saline or cell-depleted plasma. In the illustrated embodiment, the assigned maximum pressure limit for red cell concentrate may be in the range of about 300-550 mmHg, such as about 350 mmHg or other. For the less viscous, substantially cell-reduced or cell-free liquid such as saline, the assigned or selected maximum or alarm pressure limit may be in the range of about 200-400 mmHg, such as about 300 mmHg.

The lower (or first) and upper (or second) fluid flow pressure levels are, in the illustrated embodiment, based on a percentage of the maximum pressure level. By way of non-limiting example, the upper pressure level may be set, at least initially, at about 60-95%, such as about 80%, of the maximum or alarm level and the lower pressure level may be set at about 50-85%, such as about 70%, of the maximum or alarm level. Therefore, as an example only, for a maximum pressure limit of about 350 mmHg for flowing concentrated red blood cells, the lower fluid flow pressure zone or range may be pressure below about 175-300 mmHg (using 50-85% of the maximum pressure level) or below about 245 mmHg (using 70%), and the upper fluid flow pressure zone or range may be pressure that is above about 210-335 mmHg (using 60-95% of the maximum pressure level) or above about 280 mmHg (using 80%). The intermediate or buffer range or zone in this example would be from about 175-300 mmHg on the lower end and 210-335 mmHg on the upper end, for example between about 245 and 280 mmHg (using 70% and 80% respectively). While the above percentages are applicable to the illustrated embodiment, the maximum or alarm pressure may vary and the percentages or ranges can be varied without departing from the present subject matter. Also, although these percentages for defining the upper, lower and intermediate pressure ranges remain constant throughout the illustrated method, it is conceivable that these ranges can be varied during the procedure to accommodate differing flow conditions and/or subject or donor characteristics without departing from the present subject matter.

Turning now to FIG. 8, as shown there for purposes of illustration and not limitation, the system controller or processor 16 is configured, such as by programming a programmable microprocessor, to control the infusion flow path flow rate in accordance with the process and procedure set forth in the process flowchart of FIG. 8. More specifically, flow rate is controlled by controlling pump 20a, based at least in part of the fluid flow pressure within the flow path 22 sensed by pressure sensor 43a and communicated to the controller or processor 16. At the first decision step or activity 100 of the process, the controller evaluates whether the sensed pressure in the return or infusion fluid flow path is in the upper zone or range (above the second pressure level) and has remained there for a second selected period of time prior to the decision step. The system may include a timer or counter for indicating the second time period. If the pressure is in the upper zone or range (above the second pressure level) and has remained there for the second selected period of time, the process moves to processing step 102 in which the controller commands the pump 20a to reduce the flow rate of fluid in flow path 22 by the second selected amount to reduce the fluid flow pressure or limit further pressure increase. The second selected time period may be fixed or variable, and may range, as non-limiting examples, from about 2-15 seconds, such as about 3-10 seconds, or more specifically about 4-6 seconds or about 5 seconds, or more or less. The second selected amount of flow rate decrease also may be a fixed or variable amount or percentage and may, as non-limiting examples, be from about 5-20 ml/minute, such as 5-15, or 8-12 or about 10 ml/min, or more or less. Any such decrease also may be conditioned upon the flow rate being above an optionally pre-set minimum return or infusion flow rate. If the flow rate is already at the minimum flow rate, the decrease will not be implemented by the controller. The pressure levels, time periods and flow rate changes may be referred to herein with or without the word "selected" and no difference in meaning is intended.

If the flow pressure does not meet the two requirements or conditions of the first decision point, the controller proceeds to decision step 104, where it determines whether the fluid flow pressure in flow path 22 is in the lower range or zone (below the first pressure level) and whether it has remained there for at least the first selected period of time prior to the decision step. The system may include a timer or clock for indicating the first time period. If the fluid flow pressure has been in the lower range or zone for the first selected period of time, the process seeks to increase the flow rate, thereby reducing procedure time for any donor or patient and proceeds to processing step 106. At that point, the controller commands the pump 20a to increase the flow rate of fluid in flow path 22 by the first selected amount. The first selected time period employed at decision step 104 may be fixed or variable, such as, by non-limiting example, in the may range from about 10-20 seconds, such as about 13-17 seconds, or more specifically about 15 seconds or more or less. The first amount of flow rate increase also may be a fixed or variable amount or a percentage and may be less than, equal to or greater than the second selected amount of flow rate decrease and, as non-limiting example, may be from about 2-8 ml/minute, such as 4-6 or about 5 ml/min, or more or less.

In the illustrated process described above, the second selected time period for flow rate decreases is less than the first selected time period for flow rate increases and the second selected amount of flow rate decrease is greater than the first selected amount of flow rate increase. This arrangement helps to reduce the likelihood of alarm conditions due to flow reaching the maximum pressure level while also tending to reduce process times by increasing return flow rates automatically when conditions permit. The process continues to repeat or cycle through the decision steps 100 and 104 and, as called for, through processing steps 102 and 106, at a selected frequency which can be, for example, from many times per second to once every few seconds or longer. The frequency may be fixed or variable and may, for example, be from about 100 times per second to once per minute or more, such as from about 50 times per second to about 10 times per minute, or about 1-20 times per second, such as 10 times per second, or other. The steps in the process may also include sub-steps or additional decision points and/or processing steps to implement the basic overall process. One non-exclusive process that is set forth in more detail and may be employed is illustrated in FIG. 9.

Turning now to FIG. 9, the controller or processor 16 is configured, such as by programming a programmable microprocessor, to control the infusion flow path flow rate in accordance with the steps set forth in the process flowchart of FIG. 9. More specifically, and as with the process described above, the flow rate is controlled by controlling pump 20a, based at least in part of the fluid flow pressure within the flow path 22 sensed by pressure sensor 43a and communicated to the controller or processor 16. At the first decision step or activity 200 of the process, the controller evaluates whether the sensed pressure in the return or infusion fluid flow path is in the upper range, above the second pressure level, and whether a certain amount of time (the second selected amount of time) has elapsed prior to the decision. For this purpose of establishing whether the second selected amount of time has passed, the system may include a suitable clock or timer such as but not limited to a resettable counter, which is referred to in the illustrated embodiment as the "second counter." In the illustrated process, at decision step 200, the controller determines whether the timer indicates that the second selected amount of time has elapsed, which for the illustrated second counter is indicated by the counter having a count or state of zero. The role of the second counter in the illustrated embodiment will be more evident with further discussion below. If both conditions are satisfied it signifies that the fluid flow pressure in the infusion or return flow path 22 is in the upper zone or range, nearer the maximum or alarm pressure limit, and has been there for the second selected amount or period of time. The controller then commands, at processing step 202, adjustment of the pump 20a speed so that the return or infusion flow rate in the fluid flow path 22 is decreased by the second selected amount such as within the ranges described earlier for the flow rate decrease in connection with FIG. 8. Any such decrease also may be limited in whole or in part by an optionally pre-set minimum return or infusion flow rate. In addition, for a system employing a counter such as the second counter, at processing step 204 the second counter is reset to a condition other than zero, such as 1, and the system proceeds to the next decision step 206 of the process. On the other hand, if at decision step 200 either or both of the conditions is not satisfied or met, the controller proceeds immediately to the next decision step 206.

At the next decision step 206, the controller evaluates the state of the second timer or counter. If the second counter is not set to zero (e.g., it is set at 1 or more) the timer or counter is running and the condition is satisfied. For the illustrated embodiment employing the second counter, the controller adds an incremental count at processing step 208 to the second counter. The controller then proceeds to decision step 210. At decision step 210, the controller evaluates whether the second selected amount of time has elapsed. Where a counter is used, this is indicated by the number of accumulated counts, which are indicative of an amount of time. More specifically, the controller cycles though the process at a selected frequency, which may be fixed or variable, as discussed above. For example, if the controller cycles through the process at 10 times per second, an accumulation of 51 counts means that about 5 seconds (50 counts) has passed since a prior decrease of the fluid flow rate (at which time the first counter was set to "1" in processing step 204). The number of counts used in the second counter may be selected as desired relative to the chosen cycle frequency to reflect the first time period from the ranges of time periods described above—for example, the use of 100 counts at a frequency of 10 times per second, would be reflect a period of 10 seconds, but 20 counts would be 2 seconds. The cycle time or rate for the processor could of course be other than 10 times per second as used in the illustrated embodiment. If the selected number of counts representing the desired time period have not accumulated on the second counter, the processor proceeds directly to the next decision step 214. If the selected number of counts representative of the first time period discussed earlier, such as 50 counts for 5 seconds or 100 counts for 10 seconds (at a cycle frequency of 10 times per second), have accumulated, the answer is "Yes," and the processor resets the second counter to zero at processing step 212, which prepares or conditions the second counter for another possible decrease in return fluid flow rate when the system cycles through decision step 200 again.

In either case, the controller or process next proceeds to decision step 214 of the system and process where it evaluates (1) whether the fluid flow pressure in the return or infusion flow path 22 is in the lower range and (2) whether the pump 20a is pumping at the desired rate. It will be recalled that the lower pressure range, below the first or lower pressure level, is where fluid flow rate can be increased without undue concern of approaching the maximum or alarm pressure level. The condition requiring the pump to be operating at the desired rate takes into account that it requires time for the pump to change, such as ramp down or ramp up, in response to any controller commands to decrease or increase pumping speed.

If either or both of the conditions in decision step 214 is not satisfied ("No"), the controller sets another timer or clock, such as a first counter, to zero at processing step 216 and immediately cycles back to decision step 200. If both conditions are satisfied ("Yes"), meaning that the pressure level is below the lower level and the pump has completed any prior ramp up or ramp down or is otherwise pumping at the desired rate, the controller adds one count to a first counter at processing step 218 and proceeds to the decision step 220.

Decision step 220 addresses whether the first selected time has elapsed based on the timer or clock, such as the first counter. In the illustrated embodiment employing a counter, the system determines whether the first counter has accumulated the number of counts representative of the first selected time period for increasing flow rate. That time period may be, for example, within any of the ranges described earlier for the first time period or some other time period. In the illustrated embodiment, the first selected time period is 15 seconds, which is indicated by 150 counts (equal to about 15 seconds based on repeating the cycle 10 times per second). If the first selected time has not elapsed, the controller proceeds directly to decision step 200. If the first selected time period of about 15 seconds (or whatever time has been selected) has elapsed since the last flow rate adjustment, the first timer such as the first counter is restarted or reset to zero at processing step 222, the pump 20a is commanded to increase the fluid return or infusion flow rate by a selected first rate of increase, at processing step 224, and the controller or process proceeds or loops back to decision step 200 to repeat the process steps.

If the fluid flow pressure remains below the lower pressure level and the pump is at the desired flow rate (e.g., has ramped up from the prior flow rate increase), the conditions of decision steps 200 and 206 will not be satisfied, but the conditions of decision step 214 will continue to be satisfied and after the first selected time period has elapsed (e.g., the first counter has accumulated the representative number of counts), the flow rate will again be increased by the first flow rate increase, which can be in the ranges described earlier or such other rate as desired, and this will continue to be repeated so long as the conditions of decision step 214 are satisfied so as to keep the fluid flow rate as high as possible within the lower or "good" pressure range. On the other hand, if the fluid flow pressure remains above the upper level, even after a prior flow rate decrease and the second selected time period for decreases has elapsed from the prior decrease (e.g., the second counter has accumulated the representative number counts), the conditions of decision step 200 will be satisfied and the flow rate will again be decreased by the second selected rate change, or at such other rate change as is chosen, and that will be repeated once every second selected amount of time (or other selected time period) or thereabouts until the conditions of step 200 are no longer satisfied, such as when the fluid flow pressure moves below the upper pressure level and into the intermediate pressure range.

It should be noted that the infusion or return flow rates in the illustrated embodiment, even if adjusted according to the above process, will optionally not be permitted to exceed an upper flow rate limit or fall below a lower flow rate limit. The upper flow rate limit may be, for example only, the minimum of (1) the desired flow rate set by the device operator or (2) in applications where the subject is a living person, the fluid flow rate that returns the maximum allowed or tolerated rate of anticoagulant flow (e.g., citrate flow) to the subject (since blood products returned to the subject will contain some residual amount of the anticoagulant that was initially added to the withdrawn donor's blood to prevent clotting). A lower limit may be set to keep the needle or other access device in the infusion flow path open and free of clotting or for other reasons.

In addition to the features described above, the flow control system and method may optionally include one or more aspects to generate operator alarms under certain conditions. For example, in one such aspect the controller may generate an operator alert or alarm, such as an audible and/or visual signal, if the sensed pressure in the fluid flow path 22 exceeds the maximum or alarm level that was previously assigned. In addition, such an alarm may be accompanied by automatic stopping of the infusion or return pump 20a.

In accordance with another aspect, the system/method may optionally include an alert or alarm if the fluid flow pressure in the infusion or return flow path 22 exceeds a certain amount within a limited time period or if senses a rate of pressure increase that exceeds a certain limit. This may be determined, for example, by continuing to monitor the pressure and generating an alarm if a calculated slope of pressure increase, such as may be calculated by a least squares method, over a certain amount of time exceeds an alarm limit or threshold. One example of such an alarm condition is a calculated pressure increase rate slope of about 12,000 mmHg/min, although any suitable alarm condition threshold could be chosen. In the event of this type of alarm condition, it is expected that the fluid flow through the flow path normally would be stopped automatically until operator intervention to assess and/or clear the cause of the alarm, although automatic stoppage may not necessarily accompany such an alarm condition.

Other Aspects

In additional to the aspects set forth above in the Summary, the Description above and the claims that follow, there are other aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In the first aspect set forth earlier, a method is provided for controlling flow through a biological fluid processing device (such as but not limited to an apheresis device for separating blood into one or more blood components) fluid flow path, comprising: flowing fluid through the fluid flow path at a flow rate; monitoring the pressure of fluid flowing in the fluid flow path relative to at least a first (or lower) pressure and second (or upper) pressure; and (1) decreasing the fluid flow rate in the fluid flow path by a second selected amount if the monitored pressure is above a second pressure level for a second amount of time, with the second pressure level being below the maximum allowed pressure level and above the first pressure level, and (2) increasing the flow rate of fluid in the fluid flow path by a first selected amount if the monitored pressure is below the first pressure level for at least a first amount of time.

Additionally, in accordance with a second aspect of the present subject matter, which may be used with the method of the first aspect, the flow rate of fluid in the fluid flow path is not increased to a flow rate above a maximum fluid flow rate or decreased to a flow rate below a minimum fluid flow rate.

In accordance with a third aspect of the present subject matter, which may be used with the method of any of the first-second aspects, the method may include repeatedly increasing the flow rate of fluid in the fluid flow if the monitored pressure remains below the first pressure level for at least a selected amount of time after a prior flow rate increase and repeatedly decreasing the fluid flow rate in the fluid flow path if monitored pressure is above the second pressure level for a selected amount of time after a prior flow rate decrease.

In accordance with a fourth aspect of the present subject matter, which may be used with the method of any of the first-third aspects, the method may include repeating the monitoring, increasing and decreasing steps until a selected amount of fluid is flowed through the fluid flow path.

In accordance with a fifth aspect of the present subject matter, which may be used with the method of any of the first-fourth aspects, the first selected amount of flow rate increase may be less than the second selected amount of flow rate decrease.

In accordance with a sixth aspect of the present subject matter, which may be used with the method of any of the first-fifth aspects, the second amount of time may be less than the first amount of time.

In accordance with a seventh aspect of the present subject matter, which may be used with the method of any of the first-sixth aspects, the maximum, first and second pressure levels may be based at least in part on the viscosity of the fluid flowing in the fluid flow path.

In accordance with an eighth aspect of the present subject matter, which may be used with the method of any of the first-seventh aspects, the fluid flowing in the fluid flow path may comprise one or more blood components.

In accordance with a ninth aspect of the present subject matter, which may be used with the method of any of the first-seventh aspects, the fluid flowing in the fluid flow path may be substantially free of cellular blood components.

In accordance with a tenth aspect of the present subject matter, which may be used with the method of any of the second-ninth aspects the maximum fluid flow rate may not exceed the lesser of an operator-selected flow rate and a citrate tolerance flow rate In accordance with an eleventh aspect of the present subject matter, which may be used with the method of any of the first-tenth aspects, the first pressure level, second pressure level, first selected amount of flow rate decrease, the second selected amount of flow rate increase, the first amount of time and/or second amount of time may be varied while flowing fluid through the fluid flow path.

In accordance with a twelfth aspect of the present subject matter, which may be used with the method of any of the first-eleventh aspects may include stopping fluid flow in the fluid flow path if the rate of change of the pressure of fluid flowing in the fluid flow path exceeds a selected rate.

In accordance with a thirteenth aspect of the present subject matter as set forth earlier in the Summary, a durable biological fluid processing device may be provided for processing biological fluid (such as but not limited to an apheresis device for separating blood into one or more blood components) in a disposable fluid processing flow circuit of the type including a fluid flow path for directing fluid flow from the processing circuit to a subject. The device includes a pump for pumping fluid thorough the fluid flow path, a pressure sensor for monitoring fluid pressure in the flow path and a controller cooperatively associated with the pump and the pressure sensor for controlling the flow rate and pressure of fluid flowing through the fluid flow path. The controller is configured to at least: monitor the pressure of fluid flowing in the fluid flow path relative to a first pressure level and a second pressure level, decrease the fluid flow rate in the fluid flow path by a second selected amount if the monitored pressure is above the second pressure level for a second amount of time, the second pressure level being below the maximum allowed pressure level and above the first pressure level and increase the flow rate of fluid in the fluid flow path by a first selected amount if the monitored pressure is below the first pressure level for at least a first amount of time.

Additionally, in accordance with a fourteenth aspect of the present subject matter, which may be used with the device of the thirteenth aspect, the controller may configured so that the flow rate of fluid in the fluid flow path is not increased to a flow rate above a maximum fluid flow rate or decreased to a flow rate below a minimum fluid flow rate.

In accordance with a fifteenth aspect of the present subject matter, which may be used with the device of any of the thirteenth-fourteenth aspects, the controller may be configured to repeatedly increase the flow rate of fluid in the fluid flow if the monitored pressure remains below the first pressure level for at least a selected amount of time after a prior flow rate increase and repeatedly decrease the fluid flow rate in the fluid flow path if monitored pressure is above the second pressure level for a selected amount of time after a prior flow rate decrease.

In accordance with a sixteenth aspect of the present subject matter, which may be used with the device of any of the thirteenth-fifteenth aspects, the controller may be configured so that the selected amount of flow rate increase is less than the selected amount of flow rate decrease.

In accordance with a seventeenth aspect of the present subject matter, which may be used with the device of any of the thirteenth-sixteenth aspects, the controller is configured so that the second amount of time is less than the first amount of time.

In accordance with an eighteenth aspect of the present subject matter, which may be used with the device of any of the thirteenth-seventeenth aspects, the controller is configured so that the maximum, first and second pressure levels are based at least in part on the viscosity of the fluid flowing in the fluid flow path.

In accordance with a nineteenth aspect of the present subject matter, which may be used with the device of any of the thirteenth-eighteenth aspects the controller is configured so that the maximum, first and second pressure levels are based at least in part on whether the fluid flowing in the fluid flow path comprises one or more blood components or is substantially free of cellular blood components.

In accordance with a twentieth aspect of the present subject matter, which may be used with the device of any of the thirteenth-nineteenth aspects the controller is configured so that the first pressure level, second pressure level, the first amount of flow rate decrease, the second selected amount of flow rate increase, the first selected amount of time and/or second amount of time are changed while flowing fluid through the fluid flow path.

In accordance with a twenty-first aspect of the present subject matter, a disposable fluid processing circuit may be provided in cooperative association with a durable device in accordance with any of the thirteenth-twentieth aspects above, the flow circuit including a biological fluid separator and fluid flow path for directing fluid flow form the processing circuit.

In accordance with a twenty-second aspect of the present subject matter, a durable biological fluid processing device may be provided for processing biological fluid in a disposable fluid processing flow circuit of the type including a fluid flow path for directing fluid flow from the processing circuit to a subject, which device is configured to carry out the method of any of the first-twelfth aspects.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:
1. A method for controlling flow through a biological fluid processing device fluid flow path into a living subject, comprising:
flowing fluid through the fluid flow path at a flow rate;
repeatedly monitoring the pressure of fluid flowing in the fluid flow path relative to at least a low pressure level, an upper pressure level above the low pressure level and a maximum pressure level above the upper pressure level, the repeated monitoring being at a selected time interval between each monitoring cycle;

decreasing the fluid flow rate in the fluid flow path by a selected amount of decrease if the monitored pressure is continuously between the upper pressure level and the maximum pressure level for a certain amount of time greater than the selected time interval;

incrementally advancing a flow rate increase clock at each monitoring cycle if the monitored pressure is below the low pressure level and the fluid flow rate is at a desired rate;

increasing the flow rate of fluid in the fluid flow path by a selected amount of increase if the flow rate increase clock indicates that the monitored pressure has been continuously below the low pressure level for at least another amount of time greater than the selected time interval and, if so, restarting the flow rate increase clock;

restarting the flow rate increase clock if the monitored pressure is above the low pressure level, and leaving the fluid flow rate unchanged if the monitored pressure is between the low pressure level and the upper pressure level.

2. The method of claim 1 wherein the flow rate of fluid in the fluid flow path is not increased if the monitored pressure is above the maximum pressure level or decreased if the flow rate is below a minimum fluid flow rate.

3. The method of claim 1 including repeating the monitoring, increasing, decreasing and leaving steps until a selected amount of fluid is flowed through the fluid flow path.

4. The method of claim 1 in which the selected amount of increase is less than the selected amount of decrease.

5. The method of claim 1 in which the certain amount of time is less than the other amount of time.

6. The method of claim 2 in which the maximum, low and upper pressure levels are based at least in part on the viscosity of the fluid flowing in the fluid flow path.

7. The method of claim 1 in which the fluid flow rate does not exceed the lesser of an operator-selected flow rate and a citrate tolerance flow rate.

8. The method of claim 1 in which at least one of the low pressure level, upper pressure level, the selected amount of decrease, the selected amount of increase, the other amount of time and certain amount of time is varied while flowing fluid through the fluid flow path.

9. The method of claim 8 including incrementally advancing a flow rate decrease clock at each monitoring cycle if the monitored pressure is between the upper pressure level and the maximum pressure level; decreasing the fluid flow rate by the selected amount of flow rate decrease if the flow rate decrease clock indicates that the certain time period has passed and, if so, restarting the flow rate decrease clock; and restarting the flow rate decrease clock if the monitored pressure is below the upper pressure level.

10. A durable biological fluid processing device for processing biological fluid in a disposable fluid processing flow circuit of the type including a fluid flow path for directing fluid flow from the processing circuit to a living subject, the device including a pump for pumping fluid through the fluid flow path, a pressure sensor for monitoring fluid pressure in the flow path and a controller cooperatively associated with the pump and the pressure sensor for controlling the flow rate and pressure of fluid flowing through the fluid flow path, wherein the controller is configured to, at least:

repeatedly monitor the pressure of fluid flowing in the fluid flow path relative to at least a low pressure level, an upper pressure level above the low pressure level and a maximum pressure level above the upper pressure level, the repeated monitoring being at a selected time interval between each monitoring cycle:

decrease the fluid flow rate in the fluid flow path by a selected amount of decrease if the monitored pressure is continuously between the upper pressure level and the maximum pressure level for a certain amount of time greater than the selected time interval; and leave the fluid flow rate unchanged if the monitored pressure is between the low pressure level and the upper pressure level;

the controller including a flow rate increase clock operable to determine if another time period greater than the selected time interval has passed, the controller being further configured to (i) incrementally advance the flow rate increase clock at each monitoring cycle if the monitored pressure is below the low pressure level and the flow rate is at a desired rate, (ii) increase the fluid flow rate by a selected amount of flow rate increase if the flow rate increase clock indicates that the monitored pressure has been continuously below the low pressure low pressure level for at least the other time period and, if so, restart the flow rate increase clock, and (iii) restart the flow rate increase clock if the monitored pressure is above the low pressure level.

11. A durable biological fluid processing device in accordance with claim 10 wherein the controller is configured so that the flow rate of fluid in the fluid flow path is not increased if the monitored pressure is above the maximum pressure level or decreased if the flow rate is below a minimum fluid flow rate.

12. A durable biological fluid processing device in accordance with claim 10 wherein the controller is configured so that the selected amount of flow rate increase is less than the selected amount of flow rate decrease.

13. A durable biological fluid processing device in accordance with claim 10 wherein the controller is configured so that the certain amount of time is less than the other amount of time.

14. A durable biological fluid processing device in accordance with claim 10 wherein the controller is configured so that the maximum, low and upper pressure levels are based at least in part on the viscosity of the fluid flowing in the fluid flow path.

15. A durable biological fluid processing device in accordance with claim 10 wherein the controller is configured so that at least one of the low pressure level, the upper pressure level, the selected amount of flow rate decrease, the selected amount of flow rate increase, the certain amount of time and/or the other amount of time is changeable while flowing fluid through the fluid flow path.

16. A durable biological fluid processing device in accordance with claim 10 wherein the controller is configured so that the monitoring, increasing, decreasing and leaving steps are repeated until a selected amount of fluid is flowed through the fluid flow path.

17. A durable biological fluid processing device in accordance with claim 10 further comprising a disposable fluid processing flow control circuit.

18. A durable biological fluid processing device in accordance with claim 10 in which the controller is configured to incrementally advance a flow rate decrease clock at each monitoring cycle if the monitored pressure is between the upper pressure level and the maximum pressure level; decrease the fluid flow rate by the selected amount of flow rate decrease if the flow rate decrease clock indicates that the certain time period has passed and, if so, restart the flow rate decrease clock; and restart the flow rate decrease clock if the monitored pressure is below the upper pressure level.

* * * * *